(12) United States Patent
Iliff

(10) Patent No.: US 8,731,968 B1
(45) Date of Patent: May 20, 2014

(54) PANEL DIAGNOSTIC METHOD AND SYSTEM INCLUDING AUTOMATED DIAGNOSTIC ANALYSIS

(71) Applicant: Clinical Decision Support, LLC, Nashville, TN (US)

(72) Inventor: Edwin C. Iliff, La Jolla, CA (US)

(73) Assignee: Clinical Decision Support, LLC, Nashville, TN (US)

( * ) Notice: Subject to any disclaimer, the term of this patent is extended or adjusted under 35 U.S.C. 154(b) by 0 days.

(21) Appl. No.: 13/662,828

(22) Filed: Oct. 29, 2012

Related U.S. Application Data

(63) Continuation of application No. 13/280,968, filed on Oct. 25, 2011, now Pat. No. 8,301,467, which is a continuation of application No. 12/861,669, filed on Aug. 23, 2010, now Pat. No. 8,055,516, which is a continuation of application No. 10/846,165, filed on May 14, 2004, now Pat. No. 7,780,595.

(60) Provisional application No. 60/471,487, filed on May 15, 2003.

(51) Int. Cl.
*G06F 19/00* (2011.01)

(52) U.S. Cl.
USPC .......................................................... 705/3

(58) Field of Classification Search
USPC ............................................. 705/2; 600/300
See application file for complete search history.

(56) References Cited

U.S. PATENT DOCUMENTS

| | | |
|---|---|---|
| 3,970,996 A | 7/1976 | Yasaka et al. |
| 4,051,522 A | 9/1977 | Healy et al. |
| 4,220,160 A | 9/1980 | Kimball et al. |
| 4,290,114 A | 9/1981 | Sinay |
| 4,315,309 A | 2/1982 | Coli |
| 4,337,377 A | 6/1982 | Van Riper et al. |
| 4,428,381 A | 1/1984 | Hepp |
| 4,458,693 A | 7/1984 | Badzinski et al. |
| 4,465,077 A | 8/1984 | Schneider |
| 4,531,527 A | 7/1985 | Reinhold, Jr. et al. |

(Continued)

FOREIGN PATENT DOCUMENTS

| | | |
|---|---|---|
| CN | 1477581 A | 2/2004 |
| DE | 4430184 C2 | 3/1995 |

(Continued)

OTHER PUBLICATIONS

Alexander G., Health Risk Appraisal, Intern Electro J Health Edu., 2000, 3(Special): 122-137.
Applied Medical Informatics, Inc., Medical House CallTM Interactive Home Medical Guide & Symptom Analysis, Applied Medical Informatics, 1995, p. 24, Salt Lake City, UT.
Arthur D. Little, Inc., Can Telecommunications Help Solve America's Health Care Problems? Acorn Park, Cambridge, MA, Jul. 1992, pp. 1-7.
Arthur D. Little, Inc., Telecommunications: Can It Help Solve America's Health Care Problems?, Acorn Park, Cambridge, MA, Jul. 1992, pp. 1-116.
Ball et al. Eds. Computers in Health Care: Aspects of the Computer-based Patient Record, Springer Verlag, 1992, pp. 1-336.

(Continued)

*Primary Examiner* — John Pauls
(74) *Attorney, Agent, or Firm* — Suiter Swantz pc llo

(57) ABSTRACT

A system and method is disclosed for automated analysis of an automated medical diagnostic process. The system is comprised of a computing device, storage, and diagnostic analysis module configured to observe an automated medical diagnostic process from an initial patient contact to a final result of the disease for which a diagnosis and treatment is desired. In operation, the system receives diagnosis input from a plurality of automated medical diagnostic processes, the treatment advice given to a patient during the period, and the final result of the disease. Based on these inputs, the system determines a level of accuracy of the automated medical diagnostic process for possible follow on use to improve such accuracy.

12 Claims, 4 Drawing Sheets

(56) References Cited

U.S. PATENT DOCUMENTS

| | | |
|---|---|---|
| 4,606,352 A | 8/1986 | Geddes et al. |
| 4,712,562 A | 12/1987 | Ohayon et al. |
| 4,731,726 A | 3/1988 | Allen, III |
| 4,733,354 A | 3/1988 | Potter et al. |
| 4,770,189 A | 9/1988 | Shyu |
| 4,803,625 A | 2/1989 | Fu et al. |
| 4,825,869 A | 5/1989 | Sasmor et al. |
| 4,838,275 A | 6/1989 | Lee |
| 4,839,822 A | 6/1989 | Dormond et al. |
| 4,858,121 A | 8/1989 | Barber et al. |
| 4,868,763 A | 9/1989 | Masui et al. |
| 4,933,873 A | 6/1990 | Kaufman et al. |
| 4,945,476 A | 7/1990 | Bodick et al. |
| 4,962,491 A | 10/1990 | Schaeffer |
| 4,974,607 A | 12/1990 | Miwa |
| 4,975,840 A | 12/1990 | DeTore et al. |
| 5,012,411 A | 4/1991 | Policastro et al. |
| 5,012,815 A | 5/1991 | Bennett et al. |
| 5,023,785 A | 6/1991 | Adrion et al. |
| 5,030,948 A | 7/1991 | Rush |
| 5,054,493 A | 10/1991 | Cohn et al. |
| 5,084,819 A | 1/1992 | Dewey et al. |
| 5,099,424 A | 3/1992 | Schneiderman |
| 5,113,869 A | 5/1992 | Nappholz et al. |
| 5,193,541 A | 3/1993 | Hatsuwi |
| 5,196,682 A | 3/1993 | Englehardt |
| 5,228,449 A | 7/1993 | Christ et al. |
| 5,235,510 A | 8/1993 | Yamada et al. |
| 5,241,621 A | 8/1993 | Smart |
| 5,255,187 A | 10/1993 | Sorensen |
| 5,257,627 A | 11/1993 | Rapoport |
| 5,263,123 A | 11/1993 | Hayashi |
| 5,265,613 A | 11/1993 | Feldman et al. |
| 5,299,121 A | 3/1994 | Brill et al. |
| 5,307,263 A | 4/1994 | Brown |
| 5,337,752 A | 8/1994 | Reeves |
| 5,347,632 A | 9/1994 | Filepp et al. |
| 5,357,427 A | 10/1994 | Langen et al. |
| 5,377,258 A | 12/1994 | Bro |
| 5,390,238 A | 2/1995 | Kirk et al. |
| 5,404,292 A | 4/1995 | Hendrickson |
| 5,415,167 A | 5/1995 | Wilk |
| 5,418,888 A | 5/1995 | Alden |
| 5,421,343 A | 6/1995 | Feng |
| 5,435,324 A | 7/1995 | Brill |
| 5,437,278 A | 8/1995 | Wilk |
| 5,441,047 A | 8/1995 | David et al. |
| 5,442,728 A | 8/1995 | Kaufman et al. |
| 5,463,548 A | 10/1995 | Asada et al. |
| 5,471,382 A | 11/1995 | Tallman et al. |
| 5,473,537 A | 12/1995 | Glazer et al. |
| 5,481,647 A | 1/1996 | Brody et al. |
| 5,486,999 A | 1/1996 | Mebane |
| 5,517,405 A | 5/1996 | McAndrew et al. |
| 5,519,433 A | 5/1996 | Lappington et al. |
| 5,533,522 A | 7/1996 | Feng |
| 5,541,977 A | 7/1996 | Hodges et al. |
| 5,544,649 A | 8/1996 | David et al. |
| 5,553,609 A | 9/1996 | Chen et al. |
| 5,555,169 A | 9/1996 | Namba et al. |
| 5,572,421 A | 11/1996 | Altman et al. |
| 5,583,758 A | 12/1996 | McIlroy et al. |
| 5,594,638 A | 1/1997 | Iliff |
| 5,596,994 A | 1/1997 | Bro |
| 5,601,435 A | 2/1997 | Quy |
| 5,619,991 A | 4/1997 | Sloane |
| 5,622,171 A | 4/1997 | Asada et al. |
| 5,633,910 A | 5/1997 | Cohen |
| 5,642,731 A | 7/1997 | Kehr |
| 5,642,936 A | 7/1997 | Evans |
| 5,659,793 A | 8/1997 | Escobar et al. |
| 5,660,176 A | 8/1997 | Iliff |
| 5,672,154 A | 9/1997 | Sillen et al. |
| 5,675,760 A | 10/1997 | Houwen et al. |
| 5,678,562 A | 10/1997 | Sellers |
| 5,692,220 A | 11/1997 | Diamond et al. |
| 5,692,501 A | 12/1997 | Minturn |
| 5,694,939 A | 12/1997 | Cowings |
| 5,703,786 A | 12/1997 | Conkright |
| 5,711,297 A | 1/1998 | Iliff |
| 5,722,418 A | 3/1998 | Bro |
| 5,724,968 A | 3/1998 | Iliff |
| 5,724,983 A | 3/1998 | Selker et al. |
| 5,732,397 A | 3/1998 | DeTore et al. |
| 5,746,204 A | 5/1998 | Schauss |
| 5,769,074 A | 6/1998 | Barnhill et al. |
| 5,788,640 A | 8/1998 | Peters |
| 5,794,208 A | 8/1998 | Goltra |
| 5,800,347 A | 9/1998 | Skates et al. |
| 5,802,495 A | 9/1998 | Goltra |
| 5,812,984 A | 9/1998 | Goltra |
| 5,822,715 A | 10/1998 | Worthington et al. |
| 5,823,949 A | 10/1998 | Goltra |
| 5,828,943 A | 10/1998 | Brown |
| 5,832,448 A | 11/1998 | Brown |
| 5,835,900 A | 11/1998 | Fagg, III et al. |
| 5,839,430 A | 11/1998 | Cama |
| 5,862,304 A | 1/1999 | Ravdin et al. |
| 5,868,669 A | 2/1999 | Iliff |
| 5,879,163 A | 3/1999 | Brown et al. |
| 5,887,133 A | 3/1999 | Brown et al. |
| 5,897,493 A | 4/1999 | Brown |
| 5,899,855 A | 5/1999 | Brown |
| 5,908,383 A | 6/1999 | Brynjestad |
| 5,909,679 A | 6/1999 | Hall |
| 5,910,107 A | 6/1999 | Iliff |
| 5,911,132 A | 6/1999 | Sloane |
| 5,918,603 A | 7/1999 | Brown |
| 5,933,136 A | 8/1999 | Brown |
| 5,935,060 A | 8/1999 | Iliff |
| 5,940,801 A | 8/1999 | Brown |
| 5,951,300 A | 9/1999 | Brown |
| 5,953,704 A | 9/1999 | McIlroy et al. |
| 5,956,501 A | 9/1999 | Brown |
| 5,960,403 A | 9/1999 | Brown |
| 5,974,389 A | 10/1999 | Clark et al. |
| 5,976,082 A | 11/1999 | Wong et al. |
| 5,987,519 A | 11/1999 | Peifer |
| 5,997,476 A | 12/1999 | Brown |
| 6,001,060 A | 12/1999 | Churchill et al. |
| 6,022,315 A | 2/2000 | Iliff |
| 6,032,119 A | 2/2000 | Brown et al. |
| 6,032,678 A | 3/2000 | Rottem |
| 6,071,236 A | 6/2000 | Iliff |
| 6,081,786 A | 6/2000 | Barry et al. |
| 6,101,478 A | 8/2000 | Brown |
| 6,106,459 A | 8/2000 | Clawson |
| 6,113,540 A | 9/2000 | Iliff |
| 6,117,073 A | 9/2000 | Jones et al. |
| 6,144,837 A | 11/2000 | Quy |
| 6,149,585 A | 11/2000 | Gray |
| 6,151,586 A | 11/2000 | Brown |
| 6,161,095 A | 12/2000 | Brown |
| 6,167,362 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| 6,196,970 B1 | 3/2001 | Brown |
| 6,206,829 B1 | 3/2001 | Iliff |
| 6,230,142 B1 | 5/2001 | Benigno et al. |
| 6,233,539 B1 | 5/2001 | Brown |
| 6,234,964 B1 | 5/2001 | Iliff |
| 6,240,393 B1 | 5/2001 | Brown |
| 6,246,975 B1 | 6/2001 | Rivonelli et al. |
| 6,246,992 B1 | 6/2001 | Brown |
| 6,247,002 B1 | 6/2001 | Steels |
| 6,248,063 B1 | 6/2001 | Barnhill et al. |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,330,426 B2 | 12/2001 | Brown et al. |
| 6,334,778 B1 | 1/2002 | Brown |

(56) References Cited

U.S. PATENT DOCUMENTS

| | | |
|---|---|---|
| 6,368,273 B1 | 4/2002 | Brown |
| 6,375,469 B1 | 4/2002 | Brown |
| 6,379,301 B1 | 4/2002 | Worthington et al. |
| 6,381,577 B1 | 4/2002 | Brown |
| 6,468,210 B1 | 10/2002 | Iliff |
| 6,475,143 B2 | 11/2002 | Iliff |
| 6,482,156 B2 | 11/2002 | Iliff |
| 6,524,241 B2 | 2/2003 | Iliff |
| 6,527,713 B2 | 3/2003 | Iliff |
| 6,569,093 B2 | 5/2003 | Iliff |
| 6,597,392 B1 | 7/2003 | Jenkins et al. |
| 6,598,035 B2 | 7/2003 | Branson et al. |
| 6,601,055 B1 | 7/2003 | Roberts |
| 6,641,532 B2 | 11/2003 | Iliff |
| 6,687,685 B1 | 2/2004 | Sadeghi et al. |
| 6,725,209 B1 | 4/2004 | Iliff |
| 6,730,027 B2 | 5/2004 | Iliff |
| 6,746,399 B2 | 6/2004 | Iliff |
| 6,748,353 B1 | 6/2004 | Iliff |
| 6,764,447 B2 | 7/2004 | Iliff |
| 6,767,325 B2 | 7/2004 | Iliff |
| 6,770,029 B2 | 8/2004 | Iliff |
| 6,817,980 B2 | 11/2004 | Iliff |
| 6,849,045 B2 | 2/2005 | Iliff |
| 6,900,807 B1 | 5/2005 | Liongosari et al. |
| 6,903,657 B2 | 6/2005 | Kwoen |
| 6,968,375 B1 | 11/2005 | Brown |
| 7,076,437 B1 | 7/2006 | Levy |
| 7,167,818 B2 | 1/2007 | Brown |
| 7,223,235 B2 | 5/2007 | Brown |
| 7,223,236 B2 | 5/2007 | Brown |
| 7,252,636 B2 | 8/2007 | Brown |
| 7,258,666 B2 | 8/2007 | Brown |
| 7,259,681 B2 | 8/2007 | Kwoen |
| 7,264,591 B2 | 9/2007 | Brown |
| 7,297,108 B2 | 11/2007 | Iliff |
| 7,297,109 B2 | 11/2007 | Brown |
| 7,297,111 B2 | 11/2007 | Iliff |
| 7,300,402 B2 | 11/2007 | Iliff |
| 7,305,348 B1 | 12/2007 | Brown |
| 7,306,560 B2 | 12/2007 | Iliff |
| 7,310,668 B2 | 12/2007 | Brown |
| 7,320,030 B2 | 1/2008 | Brown |
| 7,344,496 B2 | 3/2008 | Iliff |
| 7,392,167 B2 | 6/2008 | Brown |
| 7,399,276 B1 | 7/2008 | Brown et al. |
| 7,516,192 B2 | 4/2009 | Brown |
| 2001/0012913 A1 | 8/2001 | Iliff |
| 2001/0039503 A1 | 11/2001 | Chan et al. |
| 2001/0053875 A1 | 12/2001 | Iliff |
| 2002/0029157 A1 | 3/2002 | Marchosky |
| 2002/0068857 A1 | 6/2002 | Iliff |
| 2002/0148477 A1 | 10/2002 | Kwoen |
| 2002/0186818 A1 | 12/2002 | Arnaud et al. |
| 2003/0036686 A1 | 2/2003 | Iliff |
| 2003/0069753 A1 | 4/2003 | Brown |
| 2003/0153819 A1 | 8/2003 | Iliff |
| 2003/0163299 A1 | 8/2003 | Iliff |
| 2003/0181790 A1 | 9/2003 | David et al. |
| 2003/0199740 A1 | 10/2003 | Iliff |
| 2003/0204415 A1* | 10/2003 | Knowlton ................ 705/2 |
| 2004/0017475 A1 | 1/2004 | Akers et al. |
| 2004/0019259 A1 | 1/2004 | Brown |
| 2004/0059200 A1 | 3/2004 | Iliff |
| 2004/0107116 A1 | 6/2004 | Brown |
| 2004/0116780 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0193377 A1 | 9/2004 | Brown |
| 2004/0199332 A1 | 10/2004 | Iliff |
| 2004/0199409 A1 | 10/2004 | Brown |
| 2004/0219500 A1 | 11/2004 | Brown |
| 2004/0249778 A1 | 12/2004 | Iliff |
| 2005/0010088 A1 | 1/2005 | Iliff |
| 2005/0010444 A1 | 1/2005 | Iliff |
| 2005/0027562 A1 | 2/2005 | Brown |
| 2005/0060194 A1 | 3/2005 | Brown |
| 2005/0080652 A1 | 4/2005 | Brown |
| 2005/0086083 A1 | 4/2005 | Brown |
| 2005/0177391 A1 | 8/2005 | Shimizu et al. |
| 2005/0228883 A1 | 10/2005 | Brown |
| 2005/0234306 A1 | 10/2005 | Schulte et al. |
| 2005/0256739 A1 | 11/2005 | Brown |
| 2005/0273359 A1 | 12/2005 | Young |
| 2005/0273509 A1 | 12/2005 | Brown |
| 2006/0004611 A1 | 1/2006 | Brown |
| 2006/0010014 A1 | 1/2006 | Brown |
| 2006/0089969 A1 | 4/2006 | Brown |
| 2006/0100910 A1 | 5/2006 | Brown |
| 2006/0135859 A1 | 6/2006 | Iliff |
| 2006/0178914 A1 | 8/2006 | Brown |
| 2006/0189853 A1 | 8/2006 | Brown |
| 2006/0234202 A1 | 10/2006 | Brown |
| 2006/0235722 A1 | 10/2006 | Brown |
| 2006/0241975 A1 | 10/2006 | Brown |
| 2006/0247951 A1 | 11/2006 | Brown |
| 2006/0247979 A1 | 11/2006 | Brown |
| 2006/0252089 A1 | 11/2006 | Brown |
| 2006/0253303 A1 | 11/2006 | Brown |
| 2006/0253574 A1 | 11/2006 | Brown |
| 2006/0253576 A1 | 11/2006 | Brown |
| 2006/0271404 A1 | 11/2006 | Brown |
| 2006/0285736 A1 | 12/2006 | Brown |
| 2006/0287889 A1 | 12/2006 | Brown |
| 2006/0287931 A1 | 12/2006 | Brown |
| 2006/0294233 A1 | 12/2006 | Brown |
| 2007/0016445 A1 | 1/2007 | Brown |
| 2007/0016446 A1 | 1/2007 | Brown |
| 2007/0016447 A1 | 1/2007 | Brown |
| 2007/0016448 A1 | 1/2007 | Brown |
| 2007/0021984 A1 | 1/2007 | Brown |
| 2007/0048691 A1 | 3/2007 | Brown |
| 2007/0055486 A1 | 3/2007 | Brown |
| 2007/0061167 A1 | 3/2007 | Brown |
| 2007/0067251 A1 | 3/2007 | Brown |
| 2007/0078681 A1 | 4/2007 | Brown |
| 2007/0094049 A1 | 4/2007 | Brown |
| 2007/0100665 A1 | 5/2007 | Brown |
| 2007/0100934 A1 | 5/2007 | Brown |
| 2007/0111176 A1 | 5/2007 | Brown |
| 2007/0118403 A1 | 5/2007 | Brown |
| 2007/0118404 A1 | 5/2007 | Brown |
| 2007/0124179 A1 | 5/2007 | Brown |
| 2007/0168226 A1 | 7/2007 | Brown |
| 2007/0168242 A1 | 7/2007 | Brown |
| 2007/0212671 A1 | 9/2007 | Brown |
| 2007/0213608 A1 | 9/2007 | Brown |
| 2007/0299321 A1 | 12/2007 | Brown |
| 2008/0004915 A1 | 1/2008 | Brown |
| 2008/0045811 A1 | 2/2008 | Iliff |
| 2008/0046268 A1 | 2/2008 | Brown |
| 2008/0051638 A1 | 2/2008 | Iliff |
| 2008/0051639 A1 | 2/2008 | Iliff |
| 2008/0051640 A1 | 2/2008 | Iliff |
| 2008/0051641 A1 | 2/2008 | Iliff |

FOREIGN PATENT DOCUMENTS

| | | |
|---|---|---|
| DE | 4430164 A1 | 2/1996 |
| EP | 0320749 A2 | 6/1989 |
| EP | 0447710 A1 | 9/1991 |
| EP | 0531889 A2 | 3/1993 |
| EP | 0643360 A2 | 3/1996 |
| EP | 0720336 A2 | 7/1996 |
| JP | 03191952 | 8/1991 |
| JP | 3202047 | 9/1991 |
| JP | 04015035 A | 1/1992 |
| JP | 4056561 | 2/1992 |
| JP | 06083847 | 3/1994 |
| JP | 06274472 | 9/1994 |
| JP | 08117210 A | 5/1996 |
| JP | 08140944 | 6/1996 |

(56) References Cited

FOREIGN PATENT DOCUMENTS

| | | |
|---|---|---|
| JP | 08164127 A | 6/1996 |
| WO | WO 93/23819 | 11/1993 |
| WO | WO 94/00817 | 1/1994 |
| WO | WO 94/06088 | 3/1994 |
| WO | WO 95/06296 | 3/1995 |
| WO | WO 95/06298 | 3/1995 |
| WO | WO 95/19604 | 7/1995 |
| WO | WO 96/22577 | 7/1996 |
| WO | WO 97/05553 | 2/1997 |
| WO | WO 98/02836 | 1/1998 |
| WO | WO 98/02837 | 1/1998 |
| WO | WO 98/40835 | 9/1998 |
| WO | WO 99/52025 | 10/1999 |
| WO | WO 00/32088 | 6/2000 |
| WO | WO 01/61616 | 8/2001 |
| WO | WO 01/85021 | 11/2001 |
| WO | WO 02/39250 | 5/2002 |
| WO | WO 02/42876 | 5/2002 |
| WO | WO 03/040879 | 5/2003 |
| WO | WO 03/040964 | 5/2003 |
| WO | WO 03/040965 | 5/2003 |
| WO | WO 03/040989 | 5/2003 |
| WO | WO 03/040990 | 5/2003 |
| WO | WO 2008/134760 | 11/2008 |

OTHER PUBLICATIONS

Barnett et al., A computer-based medical information system for ambulatory care, Proc. IEEE, 1979, Issue 67, pp. 1226-1237.

Barr et al., (Eds.) The Handbook of Artificial Intelligence, HeurisTech Press, 1982, vol. II, Chapter VIII, pp. 175-222.

Becher, Ernst, Femmeldewesen fur soziale Dienste in Entwicklungslandern, NTZ, 33:304, 1980.

Belzer et al. "Encyclopedia of Computer Science and Technology", Marcel Dekker, Inc. NY (1978) pp. 78-79 and 114-115.

Bergman, Computers make 'house calls' to patients; Harvard Community Health Plan offers computerized information service to patients, J American Hospital Association, 67(10): 52, May 20, 1993, Oct. 17, 1994.

Bischoff, A Knowledge Based System for Assisting in Differential Diagnosis of Chemically Dependent/Mentally Ill Patients, Computers in Human Services, 1992, vol. 8, Nos. 3/4, pp. 143-151.

Bortolan et al., The role of patient history in a decision support system, IEEE, Computers in Cardiology, Sep. 1990, Proceedings, pp. 257-350.

Bouhaddou et al., An interactive patient information and education system (Medical HouseCall) based on a physician expert system (Iliad), Medinfo, 1995, vol. Pt 2, Issue 8, pp. 1181-1185, Vancouver, Canada.

Bouhaddou et al., Iliad and Medical House Call: Evaluating the Impact of Common Sense. Knowledge on the Diagnostic Accuracy of a Medical Expert System, AMIA, Inc., 1995, pp. 742-746.

Bowden et al., Data structures for general practice records, Information Processing, (1972), 71:1398-1406.

Brown et al., Information Infrastructure Task Force, The National Information Infrastructure: Agenda for Action, Sep. 15, 1993, pp. 26.

Christine, The Future of Health Care Technologies, HighBeam Research, Risk Management, Nov. 1, 1992, 1-3.

Cimino et al., IEEE/Ninth Annual Conference of the Engineering in Medicine and Biology Society, 1987, "DXplain: An interactive knowledge base for assistance in medical diagnostic decisions."

Collen, Machine diagnosis from a multiphasic screening program, Proceedings of 5th IBM Medical Symposium at 131, 1963.

Common Carrier Week 8, Home Education and Health Benefits said to be underestimated, Warren Publishing Inc., Jan. 20, 1992, 9(3): 1-3.

Conrath et al., A preliminary evaluation of alternative telecommunication systems for the delivery of primary health care to remote areas, IEEE Transactions on Communications, COM-23(10):1119-1126, 1975.

Cope, For well-connected in study, computer's diagnosis is just a phone call away, Minneappolis Star Tribune, Mar. 1992, pp. 03E.

Creative Strategies International. (CSI), The Emerging Self-Help Healthcare Market—Microcomputer Applications, 1984, pp. 1-121.

Crossman, Confused? Take two aspirin and call up advisor, New Jersey Record, Apr. 1992, pp. B02.

Currid, Risky Business: doctors, lawyers shy away from computer technology, PC Week, Sep. 17, 1990.

Curtin et al. "Disease Management Information System: Design, Development, Testing, and Clinical Application for Cancer Management", Abstract http://ascobeta.infostreet.com/prof/me/html/abstracts/hre/m_1509.htm (1997).

Dahmer J., "Anamnese und Befund", Georg Thieme Verlag, 1981, pp. 22-25, 44-47, 292-295 and 371-375.

Dahmer J., Der Denkprozess "Vom Symptom zur Diagnose", Anamnese und Befund, Georg Thieme Verlag, 1981, p. 3.

Dawson, Sun, Microsoft battle over Net computing, Multichannel News, Nov. 1996.

Doheny K Hack attack, LA Times Magazine, p. 8, Aug. 4, 1991.

Ellis et al., Health Education using Microcomputers: Initial Acceptability, Preventive Medicine, Jan. 1981, 10(1): 77-84.

Ellis et al., Health Education Using Microcomputers II: One year in the Clinic; Preventive Medicine, 1982, 11: 212-224.

European Examination Report dated Apr. 11, 2005 in European Patent Application No. 02075042.8, filed Jan. 7, 2002.

European 2nd Examination Report dated Apr. 23, 2008 in European Patent Application No. 02075042.8, filed Jan. 7, 2002.

Evans, C. Edward, A Computer in the Waiting Room: Who Needs the Doctor?, Can Fam Phys., Apr. 1984, 30: 869-876.

Fallon et al., A Primer for Writing Medical Data Base for the Clinical Decision Support System, ed. Schadê et al., Computers and Brains, Progress in Brain Research, 33: 155-175, Prog Brain Res. vol. 33: pp. 155-175; 1970.

Federal Register, National Telecommunications and Information Administration, DOC—Administration Policy Statement, Notices, Sep. 21, 1993, Fed. Reg., 58(181): 49025-49036.

Fielding J, Appraising the Health of Health Risk Appraisal, Am J Pub Health, Apr. 1982, 72(4): 337 340.

First Opinion Corporation, Canadian Trademark Application File History TMA447,669, registered Sep. 15, 1995 for the Trademark/Servicemark: First Opinion, pp. 51.

Fisher et al., "Great Expectations: Expectation-based reasoning in Medical Diagnosis," Proceedings of the 12th Annual Symposium on Computer Applications in Medical Care, Nov. 6, 1988, pp. 38-42.

Frenger, Details of a database management system for a telephone medical consultation service, IEEE Frontiers of Computers in Medicine, 1982.

Frenger, Advanced techniques used to create a telephone medical consultation service, ISA, pp. 103-107, 1983.

Freudenheim, Computer says take 2 aspirin, The New York Times, Business and Health, p. D2, Jun. 25, 1991.

Gale et al., Medical Diagnosis From Student to Clinician, Oxford University Press, pp. 1-22 (1983)., Jan. 19, 2006.

Gardner, Integrated Computer Systems for Monitoring of the Critically Ill, Proceedings of 1st Annual Symposium on Computer Application in Medical Care, Washington, D.C., IEEE Computer Society, 1977, pp. 301-302.

Gini et al., A Serial Model for Computer Assisted Medical Diagnosis, Int J Bio-Medical Comp., 11: 99 113 (1980).

Goetz et al., Health Risk Appraisal: The Estimation of Risk, Health Promotion at the Worksite, Mar.-Apr. 1980, 95(2): 119-126.

Goldbard, Class Notes, Tulane Medicine, Tulane University Medical Center, 1430 Tulane Avenue, New Orleans, LA 70112-2699, p. 26, Jun. 1991.

Gome, Amanda, Herald-Sun, p. 13, Nov. 19, 1991, "A picture of success."

Gorry, G. Anthony, FA6.3 Automating Judgmental decision making in medicine, Bulletin of the Operations Research Society of America, 19(2), 1971, Abstract.

\* cited by examiner

PANEL DIAGNOSTIC METHOD AND SYSTEM INCLUDING AUTOMATED DIAGNOSTIC ANALYSIS

RELATED APPLICATIONS

This application is a continuation of U.S. application Ser. No. 13/280,968 filed Oct. 25, 2011, entitled "PANEL DIAGNOSTIC METHOD AND SYSTEM INCLUDING ACTIVE AND PASSIVE STRATEGIES", which is a continuation of U.S. Pat. No. 8,055,516 filed Aug. 23, 2010, entitled "PANEL DIAGNOSTIC METHOD AND SYSTEM", which is a continuation of U.S. Pat. No. 7,780,595 filed May 14, 2004, entitled "PANEL DIAGNOSTIC METHOD AND SYSTEM", which claims the benefit of U.S. Provisional Application No. 60/471,487, filed May 15, 2003, entitled "PANEL DIAGNOSTIC METHOD AND SYSTEM", all of which are hereby incorporated by reference in their entirety.

FIELD OF THE INVENTION

The field of the invention relates to computerized medical diagnostic systems. More particularly, embodiments of the present invention relate to a computerized system for time-based diagnosis of a patient's medical complaint by use of multiple diagnostic processes operating in parallel.

DESCRIPTION OF THE RELATED ART

A computerized method and system, including an embodiment called MDATA (Medical Diagnosis And Treatment Advice), has been described in Applicant's patents, such as Applicant's U.S. Pat. No. 5,660,176, entitled "Computerized Medical Diagnostic And Treatment Advice System", U.S. Pat. No. 5,594,638, entitled "Computerized Medical Diagnostic System Including Re-enter Function and Sensitivity Factors, and U.S. Pat. No. 5,724,968, entitled "Computerized Medical Diagnostic System Including Meta Function," each of which is incorporated by reference. The automated diagnostic system is utilized in an automated system capable of conducting a consultation with a human user who is (or represents) the patient. In a typical consultation, the user asks the automated diagnostic system to diagnose a specific medical problem. The automated diagnostic system then asks the user questions about the patient's health and ultimately generates a differential diagnosis, i.e., a list of diseases or disorders that match the case, ranked in probability order. The automated diagnostic system is fully automated: other than the online user, no other human is involved in the consultation.

The automated diagnostic system has used several different diagnostic methods (methodologies) each having their own inherent strengths and weaknesses. What is desired are enhancements to the automated diagnostic system to add one or more automated processes, each of which is capable of performing an automated medical diagnosis by itself, so that a computer runs several processes to their conclusion at the same time, with each process working on the same case.

SUMMARY OF CERTAIN INVENTIVE ASPECTS

In one embodiment there is a computerized medical diagnostic system, comprising a diagnostic module configured to interact with a patient or a healthcare professional and provide an initial differential diagnosis; a panel module in data communication with the diagnostic module, the panel module comprising a plurality of diagnostic strategy processes, each of which generates a strategy differential diagnosis, where the panel module compares at least a portion of the strategy differential diagnoses to thereby generate a panel differential diagnosis; and where the initial differential diagnosis and the panel differential diagnosis are reconciled so as to recommend an action or provide a diagnosis to the patient or the healthcare professional.

The panel module may additionally include a moderator in data communication with the one or more diagnostic strategy processes and the diagnostic module, where the moderator evaluates the results of each diagnostic strategy process and generates the panel differential diagnosis by comparing the strategy differential diagnoses and reordering the panel differential diagnosis accordingly. Each diagnostic strategy process may be assigned a weight for each one of a diagnosis associated with a selected chief complaint. Each diagnostic strategy process may be assigned a weight for each diagnosis in its differential diagnosis. The panel differential diagnosis may be reordered in decreasing levels of probability after the assigned weight is applied. The weight may be dynamic and change dependent on a position in a disease timeline for the patient, and the weight may be dynamic and change dependent on a position in a consultation timeline for the patient.

The diagnostic module may repetitively select a patient health item to be evaluated, evaluate the patient health item, and provide the results of the evaluation to the diagnostic strategy processes. The influence of at least one of the diagnostic strategy processes on the moderator may change after each patient health item is evaluated. The influence may comprise weighting. At least one strategy process may update its respective strategy differential diagnosis after each patient health item is evaluated. The diagnostic module may establish a synergy weight based on the evaluated patient health item, and provide the synergy weight to the diagnostic strategy processes so as to affect the prioritization within the strategy differential diagnoses, and the influence of at least one of the diagnostic strategy processes on the moderator may change after the synergy weight is established. Selected ones of the diagnostic strategy processes may operate in an active mode, where the selected diagnostic strategy processes are configured to select a patient health item to be evaluated by the diagnostic module, and the moderator may rank each selected patient health item based on the influence of each diagnostic strategy process operating in the active mode.

The panel module may additionally comprise a judge module in data communication with the moderator and the diagnostic module, where the judge module reconciles the initial differential diagnosis and a differing differential diagnosis of the panel. The judge module may reconcile by determining the more probable differential diagnosis based on previous performance of the panel diagnostic strategy processes, by blending the initial differential diagnosis and the differing differential diagnosis of the panel into a combined differential diagnosis, or by allowing more time to elapse so that a particular diagnosis declares itself.

The system may additionally comprise a judge module in data communication with the panel module and the diagnostic module, where the judge module may reconcile the initial differential diagnosis and a differing differential diagnosis of the panel. The judge module may reconcile by determining the more probable differential diagnosis based on previous performance of the panel diagnostic strategy processes, or by blending the initial differential diagnosis and the differing differential diagnosis of the panel into a combined differential diagnosis.

The system may store and access electronic medical records which are organized for each patient in a patient case, and where each of the diagnostic strategy processes may interface with a copy of the patient case. At least one of the diagnostic strategy processes may be concurrently executed with the diagnostic module. Convergence of the differential diagnoses among the diagnostic strategy processes and the initial differential diagnosis may add a convergence weight to a score so as to generate the diagnosis. The panel module may additionally comprise a registration interface for adding a new diagnostic strategy process to the panel module. The patient may utilize a patient proxy, and the patient proxy may not be a healthcare professional.

The action may comprise recommending that the patient consult with the diagnostic system at a future time, or the action may comprise requesting that the patient have a particular test or study performed. The test or study may be performed by a laboratory, and the test or study may include one or more types of imaging.

One diagnostic strategy process may comprise identifying a sequence of an onset of symptoms of a disease. The system may additionally comprise a data structure having weights for the diagnostic strategy processes corresponding to each one of a diagnosis associated with a selected chief complaint, where the weights are applied to a score for each of the diagnoses.

In another embodiment there is a computerized medical diagnostic method, comprising interacting with a patient or a healthcare professional via a diagnostic module to obtain patient health items; automatically obtaining an initial differential diagnosis based on the patient health items; automatically obtaining a plurality of strategy differential diagnoses based on the patient health items, each strategy differential diagnosis being obtained with different analysis criteria of the patient health items; comparing at least a portion of the strategy differential diagnoses; determining a panel differential diagnosis based on the compared differential diagnoses; and reconciling the initial diagnosis and the panel differential diagnosis so as to recommend an action or provide a diagnosis to the patient or the healthcare professional.

Comparing the differential diagnoses may comprise compiling the strategy differential diagnoses into a panel differential diagnosis list, and reordering the panel differential diagnosis list according to a predetermined criterion. The method may additionally comprise selecting the patient health item to be evaluated, evaluating the patient health item, and providing the results of the evaluation to the obtaining of differential diagnoses. The influence of at least one of the diagnostic strategy processes on the panel differential diagnosis may change after each patient health item is evaluated. The method may additionally comprise establishing a synergy weight based on the evaluated patient health item, and providing the synergy weight to the obtaining of differential diagnoses. The influence of at least one of the diagnostic strategy processes on the panel differential diagnosis may change after the synergy weight is established.

Interacting with the patient may include identifying a set of candidate diseases, and interacting with the patient may further include developing a list of patient health items to be evaluated based on the set of candidate diseases. The method may additionally comprise registering a new strategy differential diagnosis. Automatically obtaining at least one of the strategy differential diagnoses may include operating in an active mode, where one or more patient health items to be evaluated are selected, and may additionally comprise merging the selected patient health items, and ranking the merged patient health items according to the influence of each strategy differential diagnosis.

The method may additionally comprise identifying a patient proxy for the patient. Recommending the action may comprise recommending that the patient consult with the diagnostic method at a future time, and may comprise requesting that the patient have a particular test or study performed. The obtaining of strategy differential diagnoses may be concurrent with the obtaining of the initial differential diagnosis. The obtaining of a selected one of the strategy differential diagnoses may comprise identifying a sequence of an onset of symptoms of a disease.

In yet another embodiment there is a computerized medical diagnostic system, comprising means for interacting with a patient or a healthcare professional via a diagnostic module to obtain patient health items, means for automatically obtaining an initial differential diagnosis based on the patient health items, means for automatically obtaining a plurality of strategy differential diagnoses based on the patient health items, each strategy differential diagnosis being obtained with different analysis criteria of the patient health items, means for comparing at least a portion of the strategy differential diagnoses, means for determining a panel differential diagnosis based on the compared differential diagnoses, and means for reconciling the initial diagnosis and the panel differential diagnosis so as to recommend an action or provide a diagnosis to the patient or the healthcare professional.

The means for comparing the strategy differential diagnoses may comprise means for compiling the strategy differential diagnoses into a panel differential diagnosis list, and means for reordering the panel differential diagnosis list according to a predetermined criterion. The means for interacting with the patient may include means for identifying a set of candidate diseases. The means for interacting with the patient may further includes means for developing a list of patient health items to be evaluated based on the set of candidate diseases.

The system may additionally comprise means for registering a new strategy differential diagnosis. The means for automatically obtaining the plurality of strategy differential diagnoses may include means for operating in an active mode, where one or more patient health items to be evaluated are selected. The system may additionally comprise means for merging the selected patient health items, and means for ranking the merged patient health items according to the influence of each strategy differential diagnosis. Recommending the action may comprise means for recommending that the patient consult with the diagnostic method at a future time. Recommending the action may comprise means for requesting that the patient have a particular test or study performed. The means for automatically obtaining the plurality of strategy differential diagnoses may operate concurrently with the means for obtaining the initial differential diagnosis. The means for automatically obtaining the plurality of strategy differential diagnoses may comprise identifying a sequence of an onset of symptoms of a disease.

DETAILED DESCRIPTION OF CERTAIN INVENTIVE EMBODIMENTS

The following description presents certain specific embodiments of the present invention. However, the present invention may be embodied in a multitude of different ways as defined and covered by the claims. In this description, reference is made to the drawings wherein like parts are designated with like numerals throughout.

The automated diagnostic system has been enhanced to add one or more automated processes, each of which is capable of performing an automated medical diagnosis by itself, so that a computer runs several processes to their conclusion at the same time, with each process working on the same case. A Panel module in data communication with the automated diagnostic system provides these enhancements. The purpose of the additional diagnostic processes is to apply alternative diagnostic strategies to a patient's case, for several possible reasons:

- to observe the automated diagnostic system's analysis of the case at a detail level,
- to copy the case data and apply them to their own model of the case,
- to comment on the automated diagnostic system's analysis, questions, and question sequence,
- to suggest alternative questions to be asked,
- to comment on the automated diagnostic system's conclusions,
- to offer alternative conclusions,
- to indicate a degree of consent with the automated diagnostic system's conclusions,
- to generate a consensus diagnosis of their own,
- to permit comparison of diagnostic techniques for research purposes,
- to permit comparison of techniques for testing and quality assurance purposes.

Strategies

The additional diagnostic processes are called "strategies" or strategy processes (or to anthropomorphize, "panelists" or "strategists") to distinguish them from the main automated diagnostic process. Each strategy is embodied as a software object that continuously observes, accumulates information, and formulates diagnoses as the automated diagnostic system conducts a consultation. A strategy can be similar to the diagnostic loop or module described in Applicant's U.S. Pat. No. 5,935,060, entitled "Computerized Medical Diagnostic And Treatment Advice System Including List Based Processing," which is incorporated herein by reference. Each strategy process typically uses a diagnostic technique that emphasizes a different technique or mix of techniques. For example, the first strategy might simply count the number of patient symptoms that match a candidate; a second strategy might also count the number of symptoms that do not match; a third strategy might consider the time of onset of symptoms in the patient; a fourth strategy might combine counting and onset time; a fifth might allow the candidate diseases objects to dynamically select the strategy that the disease objects recommend.

The Panel Module

Figure 1:
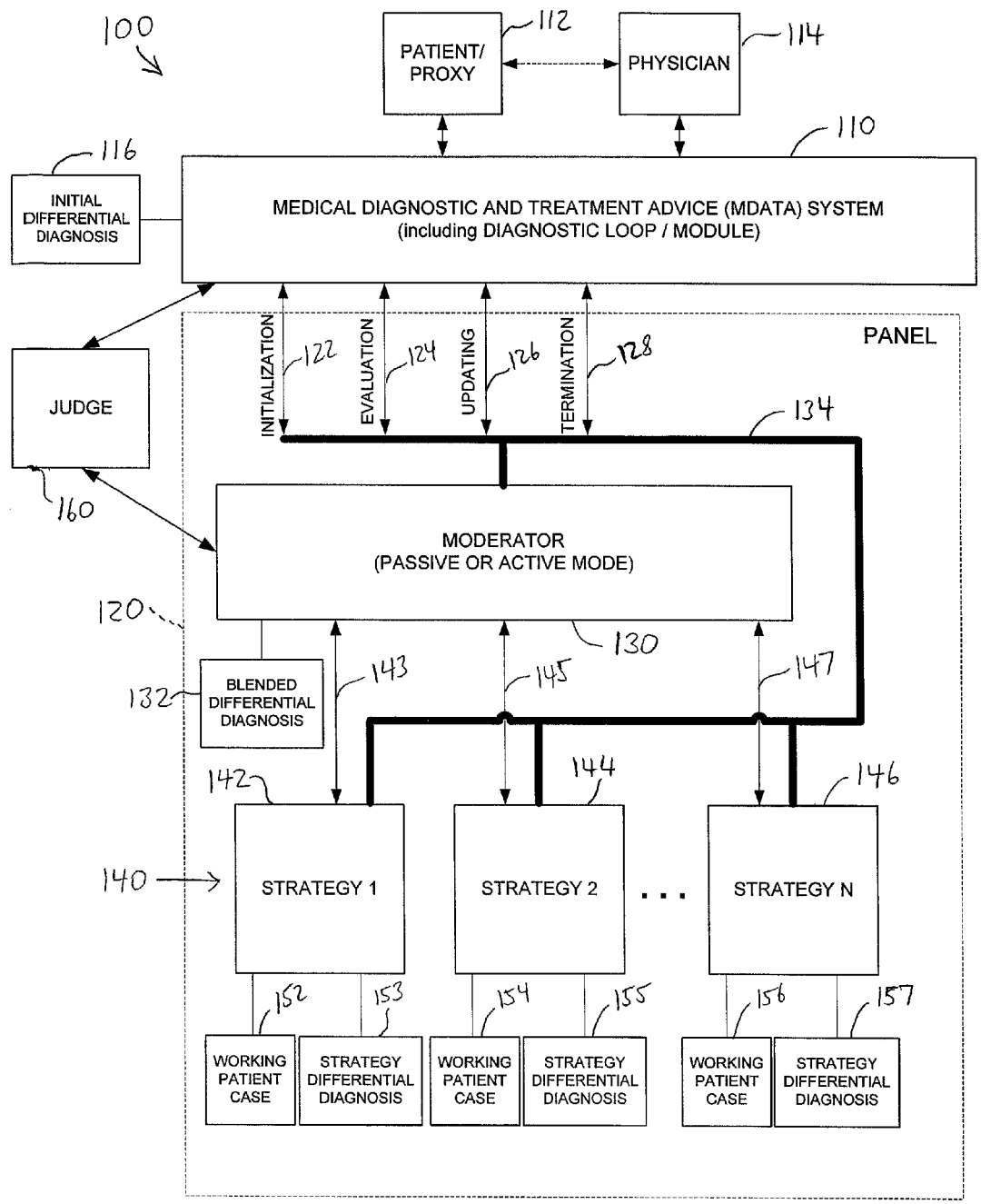
FIG. 1 is a block diagram of one embodiment of a diagnostic system incorporating a panel module.

Referring to FIG. 1, an exemplary configuration of a system 100 having a Panel module 120 will be described. The system 100 utilizes an automated diagnostic Engine 110 (e.g., Diagnostic Loop module or List-Based Processing engine), and a Panel module 120 having a Moderator 130 and "N" Panel Members 140 (Diagnosticians) or Strategy processes/objects (e.g., Strategy processes/objects 142, 144, 146), each using their own diagnostic method. The strategy processes/objects 142, 144, 146 communicate with the Moderator 130 via strategy paths 143, 145, 147, respectively. The Engine 110 handles peripheral and administrative tasks, and develops or generates an initial differential diagnosis 116 through an automated consultation or session with a patient or patient proxy 112 and/or a physician or other medical professional 114. The Moderator 130 handles internal diagnostic tasks. The Panel Members 140 conduct the consultation in parallel and develop separate differential diagnoses. The Moderator 130 coordinates the Panel Members 140, resolves conflicts, compares dynamic diagnoses, and ranks (weights) the Panel Members 140. At the end, the Moderator 130 compares all diagnoses, develops or generates a blended differential diagnosis 132, issues a consensus diagnosis, and saves the ranking of the Panel Members 140. Each Strategy process/object has its own working patient case and strategy differential diagnosis, e.g., Strategy 1 (142) has working patient case 152 and strategy differential diagnosis 153, Strategy 2 (144) has working patient case 154 and strategy differential diagnosis 155, and Strategy N (146) has working patient case 156 and strategy differential diagnosis 157.

If the main method developed by the Engine 110 and the Moderator 130 of the Panel module 120 disagree, a software object called the Judge 160 or Adjudicator is invoked to settle the issue. In FIG. 1, the Judge 160 is shown as a separate object that communicates with the Panel module 120 and the Engine or diagnostic module 110. In other embodiments, the Judge communicates with the Moderator and is part of the Panel module. The Judge 160 will be further described herein below.

Active and Passive Strategies

Strategies 140 (FIG. 1) are classified, or operate in a mode, as "passive" and "active." Passive strategies observe the automated diagnostic process 110 as it conducts the consultation, but make no comment until after the automated diagnostic process completes its diagnosis. When operating in passive mode, the automated diagnostic process 110 may communicate directly with the Panel strategies 140 via a path 134. Active strategies observe the automated diagnostic process like passive ones, but also suggest questions to be asked of the patient as the consultation is in progress. When operating in active mode, the automated diagnostic process 110 communicates with the Panel strategies 140 through the Moderator 130 and a path from the Moderator to a strategy (such as strategy 142) via a strategy path (such as path 143).

Strategy Processes

In order to qualify as such, every Panel Strategy process 140 (FIG. 1) may meet at least some portion of the following:

- compatible with the platform used by the automated diagnostic system and the Panel,
- runs without external help during a consultation,
- runs completely automatically, without human intervention,
- adheres to the run time limits and other parameters set for all strategies,
- supplies its own database and infrastructure,
- may not expect any other strategy to be present,
- communicates with the Moderator, not with the online user,
- understands the meaning and format of the automated diagnostic system patient health items (PHIs) and their values,
- generates a differential diagnosis from a given case,
- ranks the diseases of the differential diagnosis (DDx) by their probability,
- tracks incremental case changes and utilizes them in its diagnosis,
- does not have to match the DDx generated by any other strategy,
- reports its diagnosis on demand to the Moderator,
- proposes PHIs to be evaluated (active strategies only),
- explains and records its decision-making in a log.

Automated Diagnostic System/Panel Interface

In one embodiment, the diagnostic module 110 (e.g., automated diagnostic system) interfaces with the Panel module 120 at four time points during a consultation (see FIG. 1):

1) Initialization 122. When the automated diagnostic system first initializes the consultation, it calls the Moderator process 130, which initializes itself and all of the strategy processes 140 it wants to run. Initialization includes such chores as requesting computer resources, setting options, retrieving static data structures, and preparing working tables.

2) Evaluation 124. Before the automated diagnostic system, in its Diagnostic Loop, decides which PHI to evaluate next, it calls the Moderator 130 which gives active strategies a chance to suggest PHIs they would like to be evaluated.

3) Updating 126. When the automated diagnostic system, later in the Diagnostic Loop, obtains a new PHI value for the current patient, it passes the value to the Moderator 130, which incorporates it into its own copy of the case and also passes it on to all running strategies to let them update their own view of the case as well as their dynamic diagnosis. The Moderator's differential diagnosis is determined from a weighted blend of the Panel strategies in either decreasing or increasing levels of probability.

4) Termination 128. When the automated diagnostic system is about to terminate the consultation, it calls the Moderator process 130 to give it, as well as all running strategies, a chance to terminate itself as well as any running strategies.

Moderator

In one embodiment, the Panel strategy processes 140 (FIG. 1) are managed by the process called the Moderator 130 that communicates with the automated diagnostic process 110, organizes and sequences events and activities, arbitrates disputes, monitors the dynamic diagnoses as they are being developed by the various strategies, and generates its own diagnosis.

If true parallel computation is available on the platform on which the automated diagnostic system is running, then all strategies 140 execute simultaneously, while the Moderator 130 waits for all of them to complete their work. If true parallelism is not available, it can be serially simulated, with the Moderator 130 looping to give each strategy process (e.g., 142, 144) control in turn to do its work.

In one embodiment, the diagnostic module 110 (FIG. 1) such as a list-based processing method runs in parallel with the Moderator 130 and one or more diagnostic strategy functions or processes 140. The strategies 140 observe the patient consultation and develop their own diagnoses. Active strategies also suggest patient health items (PHIs) for evaluation. The Moderator 130 coordinates and ranks the strategies, and watches for "diagnostic convergence". At the end, the Moderator 130 compares all diagnoses generated by all strategies 140. The Moderator 130 generates the blended differential diagnosis 132 which is taken from all of the strategies 140. This can be based on which methodology has been more successful in the past and other things.

Figure 2:
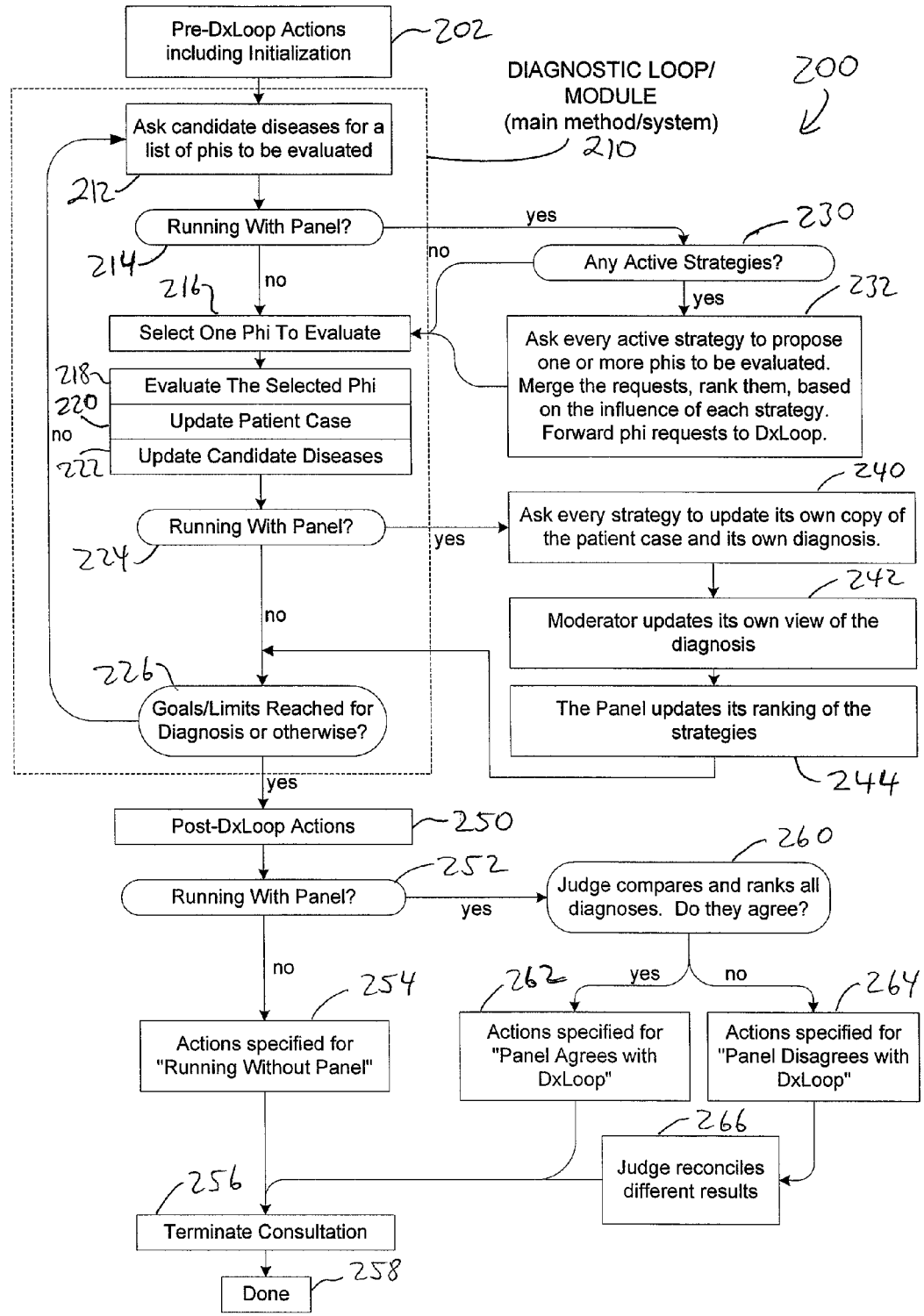
FIG. 2 is a flowchart of one embodiment of a process of operation for the system shown in FIG. 1.

Referring to FIG. 2, a flowchart of one embodiment of a process of operation 200 for the system 100 shown in FIG. 1 will be described. Beginning at a state 202, pre-diagnostic loop actions, such as initialization are performed. In one embodiment, the main automated diagnostic system and method 210 can be performed by an evaluation process or diagnostic loop (DxLoop) or diagnostic module, as described in Applicant's prior patents, such as U.S. Pat. No. 5,935,060, entitled "Computerized Medical Diagnostic And Treatment Advice System Including List Based Processing" and U.S. Pat. No. 6,468,210 (the '210 patent), entitled "Automated Diagnostic System and Method Including Synergies", which are hereby incorporated by reference. Other embodiments are described in Applicant's U.S. Pat. No. 5,660,176, entitled "Computerized Medical Diagnostic And Treatment Advice System" and U.S. Pat. No. 6,022,315, entitled "Computerized Medical Diagnostic And Treatment Advice System Including Network Access", which are also hereby incorporated by reference. The pre-DxLoop actions 202, post-DxLoop actions 250, and the test for goals/limits reached 226 are described in at least the '210 patent.

After the pre-DxLoop actions at state 202, process 200 proceeds to state 212 to ask disease objects associated with candidate diseases applicable to the patient for a list of Patient health items (PHIs) to be evaluated. PHIs are used to denote any piece or item of information that could be useful for diagnosis. For example, a PHI may be a symptom, sign, results of a laboratory test, results of a special study (like EEG), the result of an imaging modality, or the results of a particular treatment plan.

Proceeding to a decision state 214, process 200 determines if the system 100 is running with the Panel module enabled. If the system 100 is running without the use of the Panel module 120, process 200 continues at a state 216 and selects one PHI to evaluate. Without use of the Panel module 120 (FIG. 1), the diagnostic module 110 (FIG. 1) decides which of the questions proposed by the disease objects operating in the diagnostic module to ask of the patient as part of evaluating the selected PHI at state 218. The disease objects have a changing voting "strength" as the module operates due to receiving weights from four different sources or factors (as described below). The module can use rules, such as asking the questions from the critical diseases first, to determine the next question to ask.

Proceeding to state 220, process 200 updates the patient case and also updates the candidate diseases at state 222. The patient case refers to the patient medical history, consultation data, and other patient files, tables and databases for a particular patient. PHIs are stored in an electronic medical record (EMR) organized for each patient in the patient case. A medical record is created for each session and is stored in the patient's electronic medical record. In one embodiment, the patient's EMR is securely stored, such as via encryption. Transmission of the patient's EMR (or portions thereof) is performed via a secure mechanism, such as via an encrypted channel, if the EMR or portions thereof are transmitted between components of the system, e.g., between a server and patient client device. There are also certain variables that once "configured" are stored in the patient's more immediate electronic medical record—like the diagnoses he or she is carrying. Note that the system can freeze the session, so the patient may come back later to finish. A re-enter function can also be invoked to trend symptoms or to allow time to pass to see the change (evolution) of the patient's symptoms over time. Each strategy may have their own copy of the patient case as a working patient case as shown in FIG. 1. Alternatively, there may be a single case object.

Proceeding to a decision state 224, process 200 again determines if the system 100 is running with the Panel module enabled. If the system 100 is running without the use of the Panel module 120, process 200 continues at a state 226 to determine if goals and/or limits for a diagnosis or otherwise have been reached. As previously mentioned, the test for goals/limits reached is described in at least the '210 patent. Similarly, post-DxLoop actions 250 are also described in at least the '210 patent.

Proceeding to a decision state 252, process 200 again determines if the system 100 is running with the Panel module enabled. If the system 100 is running without the use of the Panel module 120, process 200 continues at a state 254 to perform actions specified for running without the Panel module. The actions specified for "running without Panel" can include reporting the diagnosis or conclusions without benefit of the Panel module. The system may operate without the Panel module notwithstanding that it is available.

The main automated diagnostic system reports the final diagnosis and/or the final differential diagnosis along with the date and time stamped record of every question, the lab test of choice, the special study of choice, the imaging modality of choice and the treatment of choice for the top n diagnoses, where n is three to five, in one embodiment. These results are reported to the physician and/or the patient (or patient proxy).

Returning to decision state 214, process 200 determines if the system 100 is running with the Panel module enabled. If the system 100 is running with the use of the Panel module 120, process 200 continues at a decision state 230 to determine if there any "active" mode strategies. If not, that is all the strategies 140 (FIG. 1) are operating in a passive mode, process 200 proceeds to state 216 to select a PHI to evaluate, as previously described. Passive mode strategies just "listen" to the questions asked by the diagnostic module and answered by the patient, and use the answers that are meaningful to each strategy to change their differential diagnosis. Passive mode strategies will be further described in conjunction with the moderator below. If there is at least one active mode strategy, as determined at decision state 230, process 200 advances to state 232. At state 232, process 200 asks every active strategy to propose one or more PHIs to be evaluated. If at least one of the strategies is operating in the active mode, the Moderator 130 (FIG. 1) looks at all of the questions that the active mode strategies want asked. Based on certain rules, the Moderator 130 selects what it thinks is the best question and passes the question (based on the PHI requests) to the diagnostic module 210 at state 216. The selection by the Moderator 130 can be done, for example, by merging the requests and ranking them based on the influence of each strategy. Active mode strategies will be further described in conjunction with the moderator below. At state 216, the diagnostic module looks at this selected question, as well as other ones that it wants to ask, and decides based on internal rules.

Returning to decision state 224, process 200 determines if the system 100 is running with the Panel module enabled. If the system 100 is running with the use of the Panel module 120, process 200 continues at state 240 and requests every strategy 140 (FIG. 1) to update its own copy of the patient case (e.g., 152 (FIG. 1)) and its own diagnosis (e.g., 153 (FIG. 1)). Advancing to state 242, process 200 directs the Moderator to update its own view of the diagnosis (e.g., 132 (FIG. 1)) and then directs the Panel module to update its ranking of the strategies at state 244. At the conclusion of state 244, process 200 advances to decision state 226 to determine if goals and/or limits have been reached, as previously described.

Returning to decision state 252, process 200 determines if the system 100 is running with the Panel module enabled. If the system 100 is running with the use of the Panel module 120, process 200 continues at a decision state 260 where a Judge object 160 (FIG. 1) compares and ranks all diagnoses, and determines if the Panel module agrees with the diagnostic module. When the Panel module agrees with the main diagnostic module, the probability that the diagnosis is established by the main diagnostic module is increased. If the main diagnostic module and the Panel module disagree, a software object called the Judge or Adjudicator is invoked to settle the issue. In FIG. 2, the Judge is shown as a separate object that communicates with the Panel module and the diagnostic module. In other embodiments, the Judge communicates with the Moderator and is part of the Panel module.

At state 262, process 200 performs actions specified for the situation when the Panel module agrees with the diagnostic module. This can include the differential diagnosis being sent to a physician or other healthcare professional, in one embodiment. Alternatively, at state 264, process 200 performs actions specified for the situation when the Panel module disagrees with the diagnostic module. This can include the system scheduling a re-enter time for the patient or patient proxy to consult the system at a later time. At the conclusion of state 264, process 200 advances to state 266 where the Judge reconciles the results of the Panel module and the diagnostic module. The Judge 160 (FIG. 1) may utilizes its rule set, which may be to decide which is more probable, blend the differential diagnoses into a common one, notify a physician, or allow more time to go by to let the disease(s) declare itself. The Judge 160 can make its decision based on the previous performance of each of the methodologies for a specific diagnosis. If, for example, the sequence of symptom onsets is very important in appendicitis, then the "weight" of the diagnosis of appendicitis from the sequence panel member (strategy) is weighted higher and may result in it being selected as the one best diagnosis for the patient.

In one embodiment, a general rule used by the Judge 160 (FIG. 1) is that the results of the diagnostic module are better than the results of the Panel module. But, the score of each disease in the diagnostic module at the end of the consultation can be key. If the score goes way over diagnostic threshold, for example if the patient has every symptom of the disease, then it gets more weight. If the strategists all have the same diagnosis and the diagnostic module has no diagnosis, then the results of the Panel module would win.

At the conclusion of either state 254, 262 or 266, process 200 performs one or more termination actions and then terminates the patient consultation at state 256. The termination actions can be as follows. The physician can review the differential diagnosis and any other records, as necessary, and provide a diagnosis to the patient. The physician may optionally also provide a prescription if necessary. In another embodiment, the results are provided directly to the patient. If a disease is diagnosed that is a chronic disease and is covered by the disease management (DM) module, the results are sent to the DM module. The DM module is described in Applicant's U.S. Pat. No. 6,234,964, which is incorporated herein by reference. In one embodiment, a report is sent to the patient and physician. A treatment in the treatment table is also determined, and a treatment report and a list of what tests to order are also sent to the physician. Process 200 completes at an end state 258.

Figure 3:
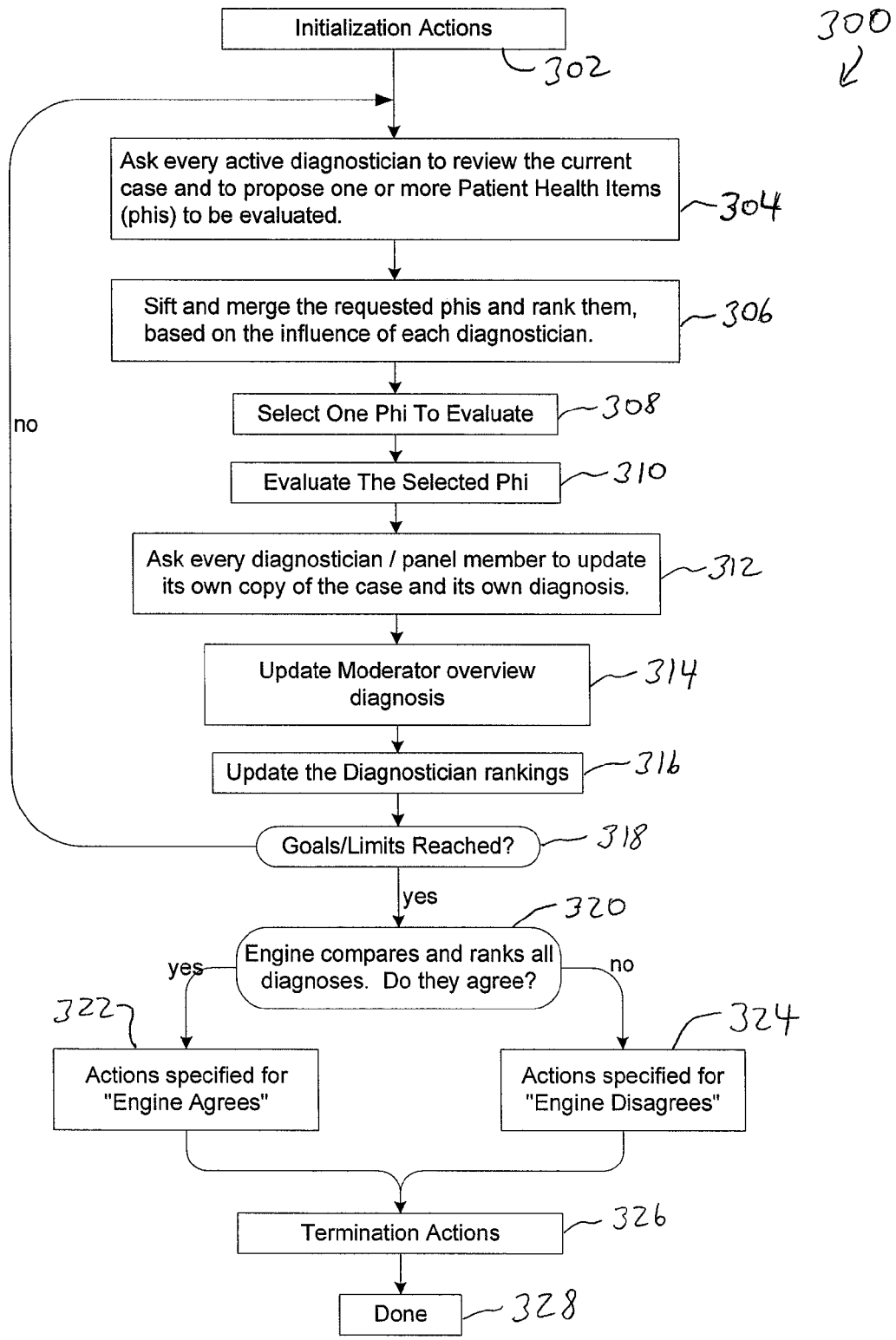
FIG. 3 is a flowchart of another embodiment of a process of operation for the system shown in FIG. 1.

Referring to FIG. 3, a flowchart of another embodiment of a process of operation 300 for the system shown in FIG. 1 will be described. Beginning at a state 302, initialization actions are performed. The initialization actions are described in at least the '210 patent. Advancing to state 304, process 300 asks every diagnostician or strategy 140 (FIG. 1) to review the current case and to propose one or more PHIs to be evaluated. Continuing at state 306, process 300 sifts and merges the requested PHIs and ranks them based on the influence of each diagnostician. Moving to state 308, process 300 selects one PHI to evaluate, and evaluates the PHI at state 310. Proceeding to state 312, process 300 requests every diagnostician or panel member to update its own copy of the case (e.g., 152 (FIG. 1)) and its own diagnosis (e.g., 153 (FIG. 1)) based on the evaluation of the PHI. Proceeding to state 314, process 300 requests the Moderator 130 to update its blended differential diagnosis 132. Continuing at state 316, process 316 updates the rankings of the diagnosticians 140. Process 300 continues at a state 318 to determine if goals and/or limits for a diagnosis or otherwise have been reached. As previously mentioned, the test for goals/limits reached is described in at least the '210 patent.

Proceeding to a decision state 320, the diagnostic module or engine 110 (FIG. 1) compares and ranks all diagnoses, and determines if the diagnoses agree. At state 322, process 300 performs actions specified for the situation when the engine determines that the diagnoses agree. This can include the differential diagnosis being sent to a physician or other healthcare professional, in one embodiment. Alternatively, at state 324, process 300 performs actions specified for the situation when the engine determines that the diagnoses disagree. This can include the system scheduling a re-enter time for the patient or patient proxy to consult the system at a later time.

At the conclusion of either state 322 or 324, process 300 performs one or more termination actions and then terminates the patient consultation at state 326. The termination actions can be as follows. The physician can review the differential diagnosis and any other records, as necessary, and provide a diagnosis to the patient. The physician may optionally also provide a prescription if necessary. In another embodiment, the results are provided directly to the patient. If a disease is diagnosed that is a chronic disease and is covered by the disease management (DM) module, the results are sent to the DM module. In one embodiment, a report is sent to the patient and physician. A treatment in the treatment table is also determined, and a treatment report and a list of what tests to order are also sent to the physician. Process 300 completes at an end state 328.

Moderator and Passive Mode

If all the strategies are operating In the passive mode, the strategies just "listen" to the questions asked by the diagnostic module and answered by the patient, and use the answers (that are meaningful to each strategy) to change their differential diagnosis. The flow of information from the diagnostic module (e.g., the main automated diagnostic system) 110 (FIG. 1) to the Panel module 120 does not have to go through the Moderator 130 as shown by the path 134.

If the information does not go through the Moderator 130 (but uses path 134), each strategist has a mechanism to take the structure of the question from the diagnostic module (list-based engine) and transform it to a format that each strategy can utilize. This can be done at the disease object level in the diagnostic module 110 such as using the list-based engine. For example, every question that is a sequence can be so tagged. Alternatively, the Moderator 130 can take each question and "transform" it to a format for each strategist.

In one embodiment, each strategist (panel member) 140 has the same differential diagnosis, but their disease objects are structured or formatted into the way their methodology works or their own appropriate form. In one embodiment, each of the strategies has its own differential diagnosis in the format that goes with its method. In one embodiment, each strategist has the same list of diseases in the differential diagnosis as the other strategists in the Panel and the diagnostic module list is also the same. But each strategist has each of its disease "objects" in a format that it can use. For example, a sequence strategist has all of the PHIs of the disease as a series of sequences of the appearance of the PHIs. The sequence strategist for appendicitis sees its disease as:

Anorexia>nausea>epigastric pain>right lower quadrant (rlq) pain>rlq tenderness, and has a weight for each sequence. In one embodiment, the appendicitis sequence strategist only scores its disease when a question is asked that is related to the sequence of onset of the symptoms or if it knows the starting times of the symptoms.

The following is an example how the appendicitis sequence strategist can configure the sequence of the onset of the symptoms (where ">" means "is followed by"):

| | |
|---|---|
| Anorexia > nausea and vomiting = | 2 points |
| Anorexia > epigastric pain = | 3 points |
| Anorexia > nausea/vomiting > epigastric pain = | 4 points |
| Epigastric pain > right lower quadrant pain = | 5 points |
| Right lower quadrant pain > right lower quadrant tenderness = | 5 points |

The sequence strategist has every disease in the differential diagnosis just as a sequence of symptoms (PHIs, symptoms, signs, imaging, lab tests, etc.). It does not have the time between the onset (inter-symptom onset intervals) but just the sequence. So when the appendicitis sequence strategist learns that anorexia is followed by nausea and vomiting, it gives its disease two points.

Moderator and Active Mode

Now consider use of the Panel 120 (FIG. 1) with active mode strategy processes. In this configuration, the strategy processes 140 are permitted to ask questions. The Moderator 130 then decides which question (associated with a PHI) to pass to the diagnostic module 110. Thus, with the Panel of active modes strategy processes, the diagnostic module then has one more input (question) to select from in addition to all of the inputs (questions) from its own disease objects.

Each PHI also receives weight from four sources or factors. The effects of these factors depend upon the chief complaint being evaluated, the location in the consultation timeline, the inherent "weight" that a strategy has in diagnosing a chief complaint, and the disease under consideration and a position in the disease timeline for the patient. Therefore, there are several sets of weights utilized: chief complaint-based, disease-based, consultation timeline based, disease timeline based.

For example, each active mode strategy looks to see what piece of information it wants (in the example above, it would want to know if epigastric pain was followed by right lower quadrant pain) and forwards this to the Moderator 130. The Moderator 130 looks at the disease objects the main diagnostic module 110 is running and determines whether there are any questions relating to right lower quadrant pain following epigastric pain. If there are, the Moderator 130 then puts this aside and looks at the next request from a strategist. At the end of this step, the Moderator 130 has all of the proposed questions of the Panel 120 and throws out all the requests that do not match a possible question of the main module disease objects.

Next, the Moderator 130 decides which question to ask based on a series of rules that it keeps. The rules could include one as follows:

"If there is a Panel request that deals with a critical disease, (reaches or exceeds a score of how critical the disease is (0 to 10 or 0 to 100)) then ask this question."

See further rules discussion below.

Moderator and Weighting of the Strategies

Just like not all PHIs are weighted the same in different diseases, the strategies 140 (FIG. 1) have a different influence on the Moderator 130 in the active mode, that is, a different influence with regard to which PHI the Moderator suggests to the main diagnostic system 110. Also, the strategies 140 have a different influence on the "blended" differential diagnosis 132 that the Moderator 130 keeps. For example, if in abdominal pain, the sequence strategy has proven to be good at getting the right diagnoses at the earliest point in time, it will have more influence over what PHI is recommended, and also the Moderator's differential diagnosis 132. In one embodiment, influence includes weighting. Please note that the strategist's weighting is dynamic and changes depending on where in the disease timeline each diagnosis is and what part of the consultation the system is in.

When a new strategy is conceived, it will be added to the Panel in a test mode. The test mode starts with the new strategy being in passive mode in one embodiment. At the end of each diagnostic session, the actual diagnosis (by the automated diagnostic system list-based engine) is compared with the diagnosis (actually differential diagnosis) of the new strategy to see how well it did. After suitable testing, it is added to the Panel officially and it is assigned a base weight for influence over the Moderator 130 in requesting PHIs (in active mode) and its weight in influencing the blended differential 132 of the Moderator. One weight depends upon what the chief complaint is, e.g., abdominal pain, and is considered to be chief complaint-based. Another weight of influence depends upon how well the strategy process has performed in the past in diagnosing the disease that is furnishing the current PHI to the Moderator and is considered to be disease-based. The weights of the strategy processes 140 in creating a blended differential are dependent upon how well each strategy process has performed in diagnosing each disease using a particular chief complaint. That is, there is a weight that applies to how well the strategy process has performed in the past in diagnosing each disease on the differential diagnosis. For example, if the new strategy is sequence, the Panel mode is active, the chief complaint is abdominal pain, it is late in the consultation timeline, and the disease is appendicitis, a weight of ten may be assigned for influencing requesting PHIs and the blended differential.

Moderator and Rules

A first set of rules includes what the Moderator 130 (FIG. 1) uses in active mode to decide which PHI should be presented to the main diagnostic module 110 as the one the Panel 120 recommends asking. The weight of the PHI that a particular strategy process wants asked is the weight to be used by the Moderator 130 to decide among the PHIs suggested by other strategy processes. This can depend upon both the chief complaint being evaluated and the current disease under consideration. The following are examples of rules the Moderator 130 could use:

If PHI is from an urgent disease, give it a weight to be "asked" as follows

If urgency is greater than 90/100 give 5 points
If urgency is between 80 and 90 give 4 points
If urgency is between 79 and 80 give 3 points Take the urgency rating and multiply it by the "strength" of this diagnostic method for this chief complaint under consideration.

Take the urgency rating and multiply it by the "strength" of each disease in the differential diagnosis (i.e., how effective the method is in each disease) as derived from a table (see below).

Figure 4:
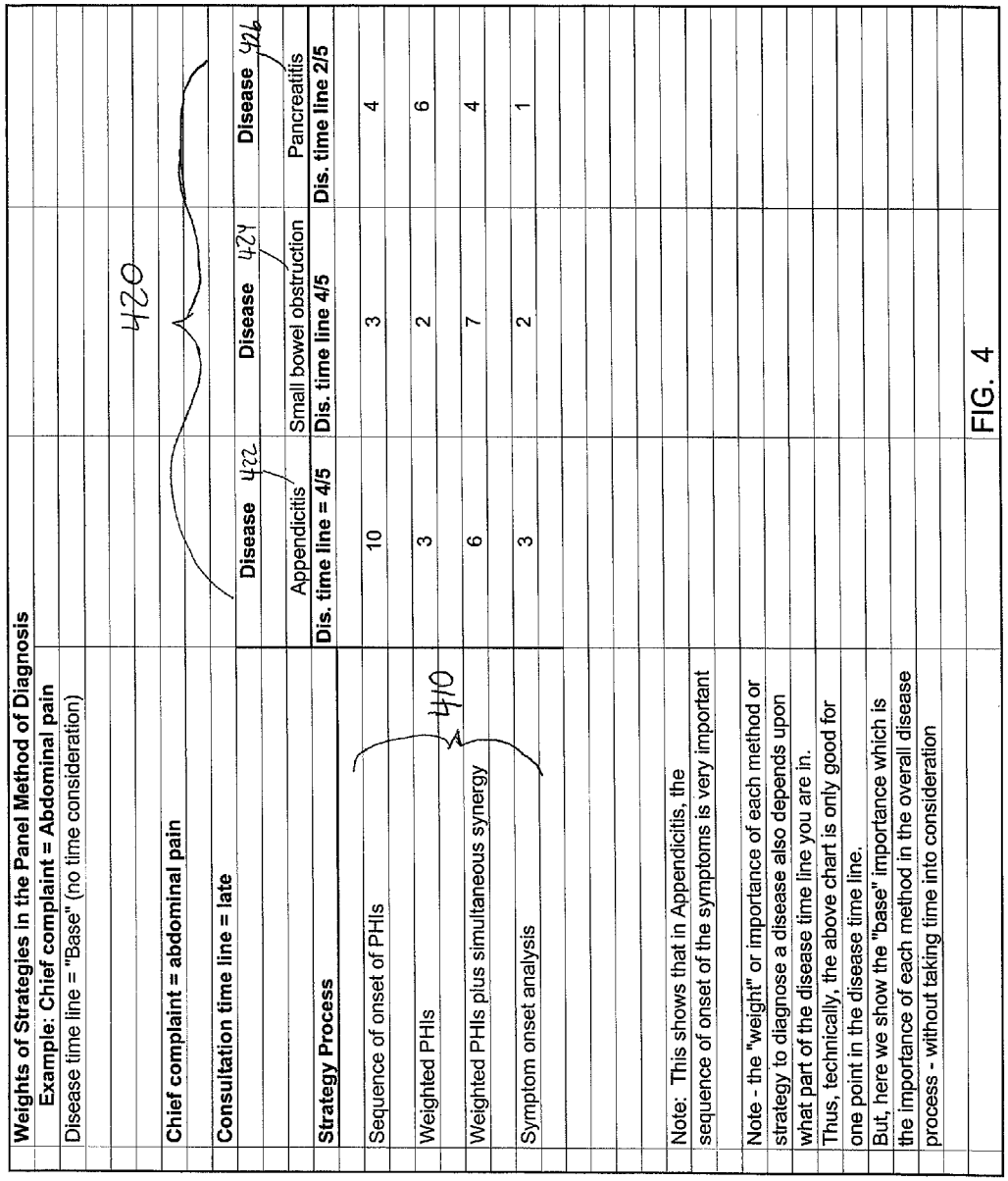
FIG. 4 is an exemplary table having weights for the importance of strategy processes for each disease in a differential diagnosis of a particular chief complaint.

Referring to FIG. 4, an exemplary table 400 having weights for the importance of strategy processes for each disease in a differential diagnosis of a particular chief complaint will be described. In the exemplary table 400 of FIG. 4, chief complaint=abdominal pain,
diseases (420)=appendicitis (422), small bowel obstruction (424), pancreatitis (426), and
numbers=the importance of each particular strategy of the group of strategies (410).

The term "base" means that the value from the table 400 pertains to the entire disease timeline for the applicable disease, without taking time into consideration. The importance of each method also changes depending upon where the patient is in on the consultation timeline and the time on the disease timeline for the disease associated with the PHI. For example, if it is later in the timeline of the consultation, the more the sequence strategy is weighted. As another example, if the appendicitis disease object is later in its timeline, a question about the presence of right lower quadrant abdominal pain is weighted much more than a question about anorexia or nausea (since these occur earlier in the disease timeline). Timelines are discussed in Applicant's U.S. Pat. No. 6,569,093, entitled "Automated Diagnostic System and Method Including Disease Timeline," which is hereby incorporated by reference.

Thus, a strategy has an overall or "base" weight on how much influence the strategy has on the Moderator 130 based upon the chief complaint being diagnosed, which, in one embodiment, is static throughout the evaluation. In addition, each disease in a strategy has a base weight of influence on the Moderator 130 based on how well that strategy has diagnosed that disease(s). Therefore, when the sequence strategist, for example, comes to appendicitis, it has more influence on the Moderator 130 to select its PHI because it has performed well in the past. Additionally, where the patient is in the consultation and where the patient is in a disease timeline (e.g., appendicitis) modify the above factors.

A second set of rules controls how much "weight" each strategist Influences the "blended" differential diagnosis 132. For example, in appendicitis, the sequence of the onset of the symptoms is very important. When the Moderator 130 comes to weighting appendicitis, it will pay more attention to the sequence strategist than another strategist. Note that, in one embodiment, the "diagnostic convergence", i.e., the extent to which the majority of strategists have one diagnosis rising on each of their differentials, is an important rule.

Because the system 100 deals with the same chief complaint and the same diseases in the differential diagnosis, the same weightings that are used in the PHI selection are used in determining the blended differential. However, one criterion that decides where each disease goes in the blended differential is how many strategists picked disease A as number one, disease B as number two, and so forth.

Moderator Actions

The Moderator 130 (FIG. 1) is a layer between the automated diagnostic system and the diagnostic strategies. As such, it is able to coordinate and integrate the actions of the various strategies 140. In one implementation, the following tasks or operations performed on or by the strategies can be sequenced and combined in different orders to gain efficiency, conserve computing resources, synchronize parallel processes, and accommodate syntax requirements. Furthermore, in various implementations, the Moderator 130 watches for diagnostic convergence. Below is a list of tasks conducted by the Moderator 130 in certain embodiments.

Task: Rank Diagnoses

The Moderator 130 asks each participating Strategy (panelist) 140 to generate a Differential Diagnosis (DDx) (e.g., 153). Each Strategy reviews the current case and uses its own special logic to generate (or update) a list of diseases in descending order of probability of being the correct diagnosis for the case. Each Strategy may have its DDx in its own appropriate form. The Strategy makes the DDx available to the Moderator 130. The Moderator 130 usually also generates or updates its own "master" DDx, and use it to make further decisions.

Task: Cross Check Rankings

The Moderator 130 uses the rankings provided by the strategies 140 as a "cross check" on the automated diagnostic process.

Task: Analyze Rankings

The Moderator 130 analyzes and compares the several DDx lists and notes:
 changes in relative position of each candidate disease,
 the degree of consensus that has been reached,
 the degree of diagnostic convergence,
 what additional information would be useful.

Task: Adjust Strategy Influence

The Moderator 130 adjusts how much "attention" it pays to each strategy. This depends on parameters such as:
 What stage the consultation is in
 What disease is being considered
 What phase the disease is in During each iteration, the "influence" or effect of each Strategy 140 is dynamically adjusted based on the "success" of that strategy. Success depends mostly on the degree of convergence, i.e., on the extent to which the Strategy advances the same disease(s) as other strategies. Thus, strategies that agree with each other will gain influence as the consultation progresses.

Task: Reward Convergence

The panel methodology uses any mix of fixed or dynamic methods, such as convergence, momentum, rate of ascent, variance, majority, weighted voting strength. The Moderator 130 may add weights to reward those strategies that are converging on a similar diagnosis or diagnostic pattern.

Task: Request Additional Data

The Moderator 130 asks each Active Strategy to propose one or more PHIs to be evaluated. Each Active Strategy looks at the current case and uses some private strategy to come up with one or more PHIs it wants to evaluate next, which it forwards as a set to the Moderator 130.

Task: Select PHIs for Evaluation

The Moderator 130 considers all of the PHIs requested by the Active Strategies, and uses some decision process to decide which PHI(s) to suggest for evaluation next, and in what order. PHIs that do not involve the online user can be evaluated at once; but PHIs that ask the online user a question need to be selected more carefully and need to be sequenced into a rational sequence.

The Moderator 130 can be impartial here, perhaps choosing the most requested PHIs, or choosing those that will statistically advance all diagnoses most effectively. Or the Moderator 130 can blatantly favor the requests of some Strategies over those of others, based perhaps on the Panel's knowledge of offline tests, or on the track records of strategies, or offline test results. For example, if a particular Strategy has proven particularly accurate when evaluating a particular chief complaint (or chief complaint syndrome) or diagnosing a particular disease, it may influence the Moderator 130 to ask the question it recommends (if in active mode) or receive more "weight" in the Moderator's blended differential diagnostic list in both active and passive modes.

Task: Synchronize Activities

Depending on the specific embodiment, the Panel module 120 may have to synchronize the activities of the various Strategies at this point. It may have to coordinate independent parallel processes, wait for the responses of the slowest Strategy, wait for the response of the online user, and handle save/recover problems on a stateless platform such as the Internet.

Task: Indicate Convergence

The Moderator 130 can indicate the extent to which the various strategy processes agree on the same diagnoses. The more rapidly the strategies have isolated one diagnosis, the more extra weight is given to that diagnosis. This diagnosis (really a differential diagnosis) is passed on to the automated diagnostic system 110 for further analysis. Note that this may not necessarily occur.

Task: Update Information

When the automated diagnostic system 110 calls the Moderator 130 with an updated item, the Moderator in turn notifies all strategies 140 to update themselves with the new PHI values. This may update:
 the Case Object (which tracks the current PHIs),
 the Consult Object (which tracks the online consultation context),
 the Patient Object (which represents the patient medical record),
 all Candidate Disease Objects (which update their scores and statuses), (usually not updated)
 all Strategy Modules (which update their separate Differential Diagnoses). Each Strategy has its diseases in the format that it uses. For example, a simple sequence Strategy has all diseases as a sequence of what PHIs usually follow each other.
 various working lists and
 tables of PHI values
 various logs such as the Consult, Backup, and Playback Log.

In one embodiment, the system 100 includes a computer program that lets a Patient log on, conducts a question/answer consultation with the patient, accumulates a Case of patient health items (PHIs), confers with diagnostic Strategists, resolves disputes with a Moderator or Judge, and iteratively builds a list of disease Candidates, ranked in the order of probability that they are the patient's disease.

Advantages of Certain Implementations

New diagnostic strategies can be introduced to the system. These can be checked against the main automated diagnostic system 110. A table is kept of what methodologies (diagnostic methods and/or strategies) are best for each diagnosis, thus giving more weight to their diagnosis. One or more diagnostic strategy objects can be integrated into the main system 110 after sufficient data has accumulated on their performance. Therefore, new strategy objects are tested before integration.

A few aspects to note include the diagnostic convergence and determining which strategies are best for which chief complaints and diseases, and at what part of a disease timeline each strategy is most useful. Weights are developed for influencing the Moderator 130 in requesting PHIs (in active mode) and for influencing the blended differential diagnosis of the Moderator.

Certain embodiments of the Panel method and system allow the strengths of different diagnostic methods to be used while significantly decreasing their weaknesses. These embodiments save time if another consultation would be necessary and lead to a higher probability of the certainty of diagnosis when the Panel diagnosis agrees with the other methodology.

CONCLUSION

Specific blocks, sections, devices, functions, processes and modules may have been set forth. However, a skilled technologist will realize that there are many ways to partition the system, and that there are many parts, components, processes, modules or functions that may be substituted for those listed above.

While the above detailed description has shown, described and pointed out the fundamental novel features of the invention as applied to various embodiments, it will be understood that various omissions and substitutions and changes in the form and details of the system illustrated may be made by those skilled in the art, without departing from the intent of the invention. The foregoing description details certain embodiments of the invention. It will be appreciated, however, that no matter how detailed the foregoing appears, the invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

The invention claimed is:

1. A computerized system for analysis of an automated medical diagnostic process, the system comprising:
   a computing device;
   a storage device operatively connected to the computing device;
   a diagnostic analysis module operating as non-transitory computer readable code embodied within said computing device, the non-transitory computer readable code comprising instructions which, when executed by the computing device perform the steps of:
      observing at least one automated medical diagnostic process associated with a patient case, the patient case beginning from a first patient question/answer consultation and continuing through at least one additional patient question/answer consultation, the at least one automated medical diagnostic process associated with at least one strategy, the at least one automated medical diagnostic process including receiving and storing at least one patient health item value;
      receiving and storing a plurality of computer based diagnoses from the at least one automated medical diagnostic process, the plurality of computer based diagnoses associated with the at least one strategy;
      receiving and storing a plurality of treatment advice offered by the automated medical diagnostic process;
      receiving and storing at least one updated patient health item value, the at least one updated patient health item value measured during the patient case;
      determining a level of accuracy of the strategy associated with the automated medical diagnostic process associated with the patient case based at least on: the plurality of computer based diagnoses, the plurality of treatment advice, the at least one patient health item value, the at least one updated patient health item value received during at least one of: the first patient question/answer consultation and the at least one additional patient question/answer consultation.

2. The computerized medical diagnostic system of claim 1, wherein said observing at least one automated medical diagnostic process associated with a patient case further comprises a detail level observation of the at least one automated medical diagnostic process, the detail level observation including:
   receiving and storing a plurality of patient health item values and a plurality of updated patient health item values; and
   comparing at least one diagnostic process with another diagnostic process based on the patient health item values and the updated patient health item values.

3. The computerized medical diagnostic system of claim 1, wherein said patient case further comprises a continuing care as part of a disease management system throughout a lifetime of the patient.

4. The computerized medical diagnostic system of claim 1, wherein said plurality of computer based diagnoses further comprises one of: a diagnosis by a panel diagnostic module, a panel differential diagnosis by a moderator, and a reconciled differential diagnosis by a judge module.

5. The computerized medical diagnostic system of claim 1, wherein said receiving and storing a plurality of treatment advice offered by the automated medical diagnostic process further comprises receiving and storing at least the plurality of treatment advice offered by the automated medical diagnostic process during the at least one additional patient question/answer consultation.

6. The computerized medical diagnostic system of claim 1, wherein said at least one updated patient health item value further comprises a measurement of one of: a symptom, an objective measurement and a subjective measurement.

7. A method for computerized analysis of an automated medical diagnostic process, the method operable within a computer device or processor and comprising:
   observing at least one automated medical diagnostic process associated with a patient case, the patient case beginning from a first patient question/answer consultation and continuing through at least one additional patient question/answer consultation, the at least one automated medical diagnostic process associated with at least one strategy, the at least one automated medical diagnostic process including receiving and storing at least one patient health item value;
   receiving within the computer device and storing in a data storage operatively connected to the computing device, a plurality of computer based diagnoses from the at least one automated medical diagnostic process;
   receiving within the computer device and storing in the data storage, a plurality of treatment advice offered by the automated medical diagnostic process;
   receiving within the computer device and storing in the data storage, at least one updated patient health item value, the at least one updated patient health item value measured during the patient case;
   determining a level of accuracy of the strategy associated with the automated medical diagnostic process associated with the patient case based at least on: the plurality of computer based diagnoses, the plurality of treatment advice, the at least one patient health item value, the at least one updated patient health item value received during at least one of: the first patient question/answer consultation and the at least one additional patient question/answer consultation.

8. The method for computerized analysis of an automated medical diagnostic process of claim 7, wherein said observing at least one automated medical diagnostic process associated with a patient case further comprises a detail level observation of the at least one automated medical diagnostic process, the detail level observation including:

receiving and storing a plurality of patient health item values and a plurality of updated patient health item values; and comparing at least one diagnostic process with another diagnostic process based on the patient health item values and the updated patient health item values.

9. The method for computerized analysis of an automated medical diagnostic process of claim 7, wherein said patient case further comprises a continuing care as part of a disease management system throughout a lifetime of the patient.

10. The method for computerized analysis of an automated medical diagnostic process of claim 7, wherein said plurality of computer based diagnoses further comprises one of: a diagnosis by a panel diagnostic module, a panel differential diagnosis by a moderator, and a reconciled differential diagnosis by a judge module.

11. The method for computerized analysis of an automated medical diagnostic process of claim 7, wherein said receiving and storing a plurality of treatment advice offered by the automated medical diagnostic process further comprises receiving and storing the plurality of treatment advice offered by the automated medical diagnostic process during the at least one additional patient question/answer consultation.

12. The method for computerized analysis of an automated medical diagnostic process of claim 7, wherein said at least one updated patient health item value further comprises a measurement of one of: a symptom, an objective measurement and a subjective measurement.

\* \* \* \* \*